(12) United States Patent
Agarwal

(10) Patent No.: US 9,345,258 B2
(45) Date of Patent: May 24, 2016

(54) SYNERGISTIC PHYTOCHEMICAL COMPOSITION AND A PROCESS FOR PREPARATION THEREOF

(75) Inventor: Amit Agarwal, Karnataka (IN)

(73) Assignee: Natural Remedies PVT Ltd. (IN)

( * ) Notice: Subject to any disclaimer, the term of this patent is extended or adjusted under 35 U.S.C. 154(b) by 0 days.

(21) Appl. No.: 13/594,128

(22) Filed: Aug. 24, 2012

(65) Prior Publication Data

US 2013/0053339 A1    Feb. 28, 2013

(30) Foreign Application Priority Data

Aug. 25, 2011   (IN) .......................... 2906/CHE/2011

(51) Int. Cl.
| | | |
|---|---|---|
| *A61K 31/715* | (2006.01) | |
| *A61P 19/02* | (2006.01) | |
| *A61P 29/00* | (2006.01) | |
| *A23L 1/30* | (2006.01) | |
| *A61K 36/9066* | (2006.01) | |

(52) U.S. Cl.
CPC ........... *A23L 1/3002* (2013.01); *A61K 36/9066* (2013.01)

(58) Field of Classification Search
CPC .......................... A61K 36/9066; A23L 1/3002
USPC .......................................................... 514/54
See application file for complete search history.

(56) References Cited

U.S. PATENT DOCUMENTS

| | | | | |
|---|---|---|---|---|
| 6,224,871 B1 * | 5/2001 | Hastings et al. | ......... | 424/195.17 |
| 2008/0193573 A1 * | 8/2008 | Gow et al. | ..................... | 424/756 |

OTHER PUBLICATIONS

Clegg et al. "Glucosamine, Chondroitin Sulfate, and the two in Combination for Painful Knee Osteoarthritis", The New English Journal of Medicine (2006) vol. 354, No. 3, pp. 798-308.
Sharma et al. An Epidemiological Study of Correlates of Osteo-Arthritis in Geriatric Population of UT Chandigarh Indian J of Community Medicine (2007) vol. 32, No. 1.
Conaghan. "Osteoarthritis—National clinical guideline for care and management in adults". Retrieved on Apr. 29, 2008.
MMWR Morb Mortal Wkly Rep. (2001) vol. 50, No. 7, pp. 120-125.
Green GA Abstract. "Understanding NSAIDs: from aspirin to COX-2". Clin Cornerstone (2001), vol. 3, No. 5, pp. 50-60. PMID 11464731.
Hospitalizations for Osteoarthritis Rising Sharply. Newswise. Retrieved on Sep. 4, 2003.
Akram et al. "Curcuma longa and curcumin : A review article" Rom. J. Biol. Plant Biol., (2010) vol. 55, No. 2, pp. 65-70.
Jurenka. "Anti-inflammatory properties of curcumin, a major constituent of curcuma longa : A review of preclical and clinical research", Alternative Medicine Review (2009), vol. 14, No. 2, pp. 141-153.
Taylor et al. "*Curcumin for inflammatory bowel disease : A review of human smiles*". Alternative Medicine Review, (2011), vol. 16, No. 2, pp. 152-156.
Yue et al. "Immunostimulatory activities of polysaccharide extract isolated from Curcuma longa." Int J Biol Macromol. (2010) vol. 47, No. 3, pp. 342-347.
Gonda et al. Abstract: "Arabinogalactan core structure and immunological activities of ukonan C, an acidic polysaccharide from the rhizome of Curcuma longa". Biol Pharm Bull. (1993). vol. 16, No. 3, pp. 235-238.
Gonda et al. Abstract. "The cure structure of ukonan A, a phagocytosis-activating polysaccharide from the rhizome of Curcuma longa, and immunological activities of degradation products", Chem Pharm Bull (Tokyo), (1992) vol. 40, No. 4, pp. 990-993.
Gonda et al. Abstract "Characterization of a neutral polysaccharide having activity on the reticuloendothelial system from the rhizome of Curcuma longa", Chem Pharm Bull (Tokyo), (1992), vol. 40, No. 1, pp. 185-188.
Gonda et al. Abstract "Characterization of polysaccharides having activity on the reticuloendothelial system from the rhizome of Curcuma longa", Chem Pharm Bull (Tokyo), (1990), vol. 38, No. 2. pp. 482-486.

* cited by examiner

*Primary Examiner* — Clinton Brooks
*Assistant Examiner* — Yih-Horng Shiao
(74) *Attorney, Agent, or Firm* — Lerner, David, Littenberg, Krumholz & Mentlik, LLP

(57) ABSTRACT

The present invention provides a synergistic phytochemical composition from *Curcuma longa* possessing analgesic and anti inflammatory activity used for management of chronic pain and treatment of osteoarthritis. The composition comprises *Curcuma longa* oil and *Curcuma longa* water extract. The relative amounts of these materials may be 0.5-5% by weight and 95-99.5% by weight respectively; and optionally pharmaceutically acceptable excipients.

The present invention also provides a process for preparing the composition.

16 Claims, 5 Drawing Sheets

SYNERGISTIC PHYTOCHEMICAL COMPOSITION AND A PROCESS FOR PREPARATION THEREOF

FIELD OF THE INVENTION

The present invention relates to a synergistic phytochemical composition useful for management of chronic pain and a process for preparing the composition.

BACKGROUND OF THE INVENTION

Physical disability and poor health often accompany knee osteoarthritis (OA, joint pains), particularly as people age. This decline in function and quality of life is a complex phenomenon associated with numerous factors including pain, poor physical fitness, obesity, co-morbidity, low self-efficacy and lower extremity impairments. In addition to the functional losses associated with knee OA (joint pain) and aging, low levels of daily physical activity and exercise are common problems in this population for whom arthritis (joint pains) is a major reason for activity limitation. Osteoarthritis is the most common type of arthritis, affecting 20 million people in America alone (Daniel O et al: 2006).

Community survey data in rural and urban areas of India shows the prevalence of osteoarthritis to be in the range of 17-60.6% (M K Sharma et al; 2007).

Osteoarthritis (OA), also known as degenerative arthritis or degenerative joint disease, is a clinical syndrome in which low-grade inflammation results in pain in the joints, caused by abnormal wearing of the cartilage that covers and acts as a cushion inside joints and destruction or decrease of synovial fluid that lubricates those joints. As the bone surfaces become less protected by cartilage, the patient experiences pain upon weight bearing, including walking and standing. Due to decreased movement because of the pain, regional muscles may atrophy, and ligaments may become more lax. OA is the most common form of arthritis (Conaghan et al., 2008), and the leading cause of chronic disability in the United States, *MMWR Morb Morta*, 2008.

OA affects nearly 21 million people in the United States, accounting for 25% of visits to primary care physicians, and half of all NSAID (Nonsteroidal Anti-Inflammatory Drugs) prescriptions. It is estimated that 80% of the population will have radiographic evidence of OA by age 65, although only 60% of those will be symptomatic. (Green G A (2001). "Understanding NSAIDs: from aspirin to COX-2". *Clin Cornerstone* 3 (5): 50-60. PMID 11464731) In the United States, hospitalizations for osteoarthritis soared from about 322,000 in 1993 to 735,000 in 2006. (Hospitalizations for Osteoarthritis Rising Sharply Newswise, Retrieved on Sep. 4, 2008.)

Symptoms of OA: Joint pain, morning stiffness lasting less than 30 minutes, joint instability or buckling, loss of function.

Signs of OA: Bony enlargement at affected joints, limitation of range of motion crepitus on motion, pain with motion, malalignment and/or joint deformity.

Current Management

Current treatment for OA is relatively limited. As there are currently no pharmacological agents capable of retarding or preventing the disease. Treatment is predominantly focused on relief of pain, and maintenance of quality of life and functional independence.

Aside from weight reduction and avoiding activities that, exert excessive stress on the joint cartilage, there is no specific treatment to halt cartilage degeneration or to repair damaged cartilage in osteoarthritis. The goal of treatment in osteoarthritis is to reduce joint pain and inflammation while improving and maintaining joint function.

The first line of drug treatment is with analgesics and non-steroidal anti-inflammatory drugs (NSAIDS). Only a few of these NSAIDS are readily available as OTC products from pharmacies without prescription as potential treatments for the pain and for other pain-syndromes. Standard references to the therapy of painful inflammatory disease attest to both the efficacy and adverse effects of these particular NSAIDs.

Pharmacological Therapy

1. Analgesic Agents

Several studies have shown acetaminophen to be superior to placebo and equivalent to non steroidal anti-inflammatory agents (NSAIDs) for the short-term management of OA pain. At present acetaminophen (up to 4,000 mg/daily) is the recommended initial analgesic of choice for symptomatic OA. However, many patients eventually require NSAIDs or more potent analgesics to control pain. Oral glucosamine and chondroitin sulfate have been shown (each individually) to have a mild to moderate analgesic, effect in several double-blind, placebo-controlled studies.

2. COX-2 Inhibitors

Cyclooxygenase-2 (COX-2) inhibitors are a class of non steroidal anti-inflammatory agents (NSAIDs) that received Food and Drug Administration (FDA) approval. These specific COX-2 inhibitors appear to be as effective as current non-selective NSAIDs in treating the pain and inflammation of arthritis. Their theoretical advantage, however, is that they will cause significantly less toxicity than conventional NSAIDs, particularly in the GI tract. Non steroidal anti-inflammatory drags (NSAIDs) exert their anti-inflammatory effect primarily by inhibiting an enzyme called cyclooxygenase (COX), also known as prostaglandin (PG) synthase. COX catalyzes the conversion of the substrate molecule, arachidonic acid, to prostanoids. Prostanoids consist of prostaglandins E, D and $F_{2\alpha}$, prostacyclin and thromboxane. The major inflammatory vasoactive prostanoids are $PGE_{2\alpha}$ and prostacyclin. Thromboxane is critical for platelet clotting, while $PGD_2$ is involved in allergic reactions and $PGF_{2\alpha}$ in uterine contraction.

In addition to their inflammatory potential, prostaglandins also contribute to important homeostatic functions, such as maintenance of the gastric lining, renal blood flow, and platelet aggregation. Reduction of prostaglandin levels in these organs can result in the well-recognized side effects of traditional non-selective NSAIDs—that is, gastric ulceration, renal insufficiency, and prolonged bleeding time. The elderly are at higher risk for these side effects. For example, adults over the age of 60 who are taking NSAIDs have a 4-5 fold higher risk of gastrointestinal bleeding or ulceration then their age-matched counterparts. Other risk factors for NSAID-induced GI bleed include prior peptic ulcer disease and concomitant steroid use. Potential renal toxicities of NSAIDs include azotemia, proteinura, and renal failure requiring hospitalization. Hematologic and cognitive abnormalities nave also been reported with several NSAIDs. Therefore, in elderly patients, and those with a documented history of NSAID-induced ulcers, traditional non-selective NSAIDs should be used with caution, usually in lower dose and in conjunction with a proton pump inhibitor. Renal function should be monitored in the elderly.

3. Local Analgesic Agents

Local analgesic therapies include topical capsaicin and methyl salicylate creams. Occasionally in late stage disease, patients will require narcotic, analgesics to control pain.

4. Intra Articular Therapies

Judicious use of intra-articular glucocorticoid injections is appropriate for OA patients who cannot tolerate, or whose pain is not well controlled by, oral analgesic and anti-inflammatory agents. Periarticular injections may effectively treat bursitis or tendonitis that can accompany OA. The need for four or more intra-articular injections suggests the need for orthopedic intervention. Intraarticular injection of hyaluronate preparations has been demonstrated in several small clinical trials to reduce pain in OA of the knee. These injections are given in a series of 3 or 5 weekly injections (depending on the specific preparation) and may reduce pain for up to 6 months in some patients.

Non-pharmacological Management includes Weight reduction. Exercise/resistive strengthening.

Side Effects of Current Therapies

Analgesics: These agents are not recommended for prolonged use because they cause constipation and increase the risk of felling, particularly in the elderly.

NSAID: The most common side effects are dyspepsia, diarrhea, abdominal pain, gastric ulceration, renal insufficiency, and prolonged bleeding time.

PRIOR ART

*Curcuma longa* Linn., commonly known as turmeric is a plant that belongs to the family Zingiberaceae. Its rhizome is widely used in indigenous medicine and as part of household remedies.

It is also applied in poultices to relieve pain and inflammation.

The rhizomes contain curcumin, a yellow colored phenolic pigment which is considered as the main active constituent. In purified extracts of *C. longa* about 70 to 76% of curcumin is present, along with about 16% demethoxycurcumin and 8% bisdemethoxycurcumin. Studies have demonstrated a wide spectrum of therapeutic effects, such as anti-inflammatory, antioxidant, antitumor, antibacterial, antifungal, antiviral, anti-spasmodic, immunomodulatory and hepatoprotective activities for this plant and curcuminoids. Recently its potential utility in acquired immune deficiency syndrome (AIDS) has been demonstrated. The rhizomes also contain oil comprising of a set of constituents known as turmerones which have also been shown to possess anti-inflammatory activity. Preclinical (in vivo and in vitro), toxicological and clinical studies have been carried out and the plant is found to be safe and effective. (Akram, et al., 2010, Julie, et al., 2009 and Rebecca. 2011).

Some of the polysaccharides isolated from the plant have shown modulatory effects on release of cytokines in peripheral blood mononuclear cells (PBMC) and on reticulo endothelial systems. (Yue, et al., 2010, Gonda, et al., 1993, Gonda, et al, 1992 a, Gonda, et al., 1992 b and Gonda, et al. 1990).

The currently available herbal products which are meant for relieving pain are not very effective. Other available options in medical treatments aim at reducing the pain in patients with osteoarthritis including analgesics and anti-inflammatory drugs used in current therapeutic regimes have suboptimal reduction in pain and are associated with variety of side effects. There is therefore a need for new herbal products which are safe and highly effective against osteoarthritic pain.

SUMMARY OF THE INVENTION

In order to alleviate the drawbacks of the various methods for treating osteoarthritis available in the prior art, the applicant, has developed a novel synergistic phytochemical composition from *Curcuma longa* comprising water extract of *Curcuma longa* and *Curcuma longa* oil. Such fractions devoid of curcuminoids having enriched polysaccharide fraction, possess anti-inflammatory and immunostimulatory activity in in-vitro assay models and particularly advantageous effects are exhibited when they are blended in specific proportions.

The present invention also provides a process for preparation of the synergistic phytochemical composition of the invention.

The present invention further provides functional foods comprising the phytochemical composition.

DETAILED DESCRIPTION OF THE INVENTION

Figure 1:
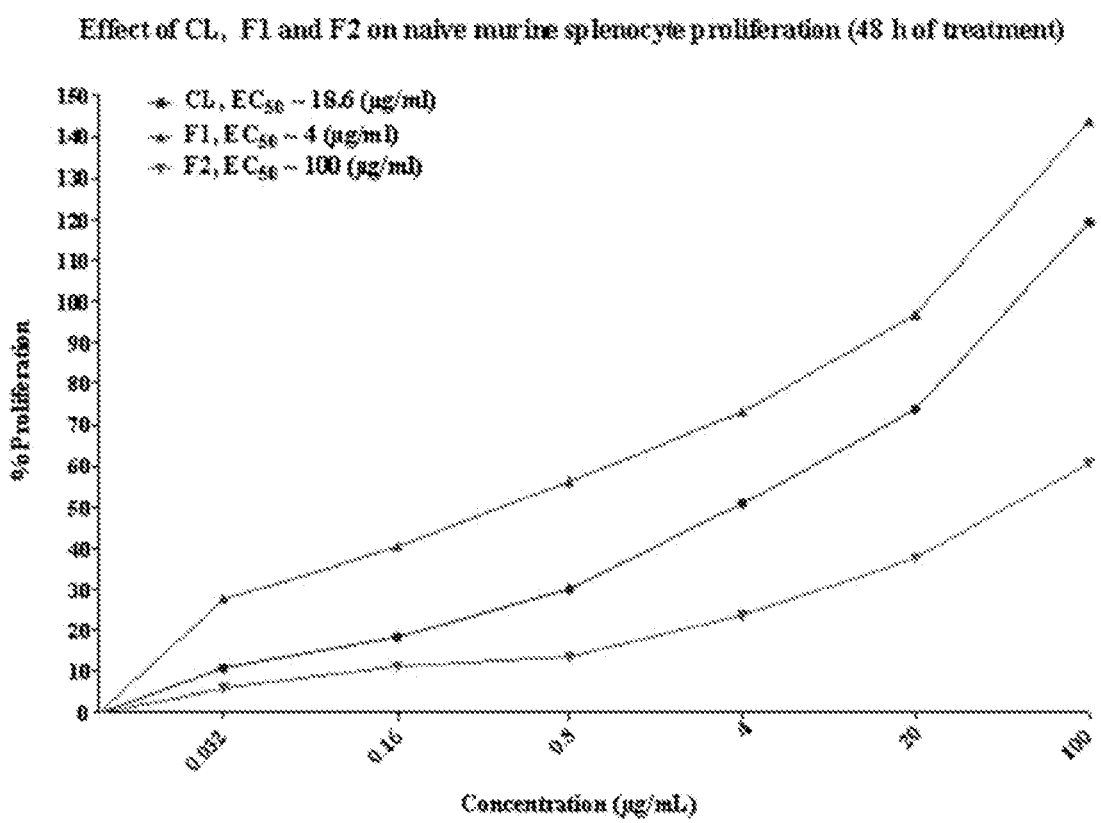
FIG. 1: Effect of CL, F1 and F2 on naive murine splenocyte proliferation.

The present invention provides a synergistic phytochemical composition possessing analgesic, immunostimulatory and anti inflammatory activity. The composition comprises a mixture of *Curcuma longa* water extract and *Curcuma longa* oil.

The relative amounts of the *Curcuma longa* oil and the *Curcuma longa* water extract, preferably are from 0.5-5% by weight and 95-99.5% by weight, respectively. The composition optionally may contain pharmaceutically acceptable excipients.

The relative amounts more preferably are:

*Curcuma longa* oil 1% by weight;

*Curcuma longa* water extract 99% by weight.

The pharmaceutically acceptable excipients of the composition are selected from a group comprising granulating agents like binding agents (Eg: Poly vinyl pyrrolidone (PVP) and Starch), lubricating agents (Eg: Magnesium stearate and talc), disintegrating agents (Eg: Cross carmellellose sodium and Crospovidone), sweetening agents (Eg: Mannitol and sucrose), coloring agents (Eg: Sunset yellow and Tartruzine), flavoring agents (Eg: Wild cherry, Vannila and Mint), coating agents (Eg: shellac and Hydroxy propyl paraben), plasticizers (Eg: Glycerin, Sorbitol and Mineral oil), preservatives (Eg: Methyl patraben and Propyl paraben), suspending agents (Eg: Carboxy methyl cellolose sodium and Guar gum), emulsifying agents (Eg: Acacia and Methyl cellulose) and spheronization agents (Eg: Micro crystalline cellulose and Carboxy methyl cellulose sodium).

The composition of the present invention may be formulated into a wide range of dosage forms selected from the group comprising tablets, troches, lozenges, water or oily suspensions, dispersible powders or granules, emulsion in hard or soft gel capsules, syrups, elixirs, phytoceuticals. neutraceuticals and food stuffs by mixing with GRAS (Generally Regarded As Safe) grade of pharmaceutical excipients to prepare various dosage forms like capsules, tablets, syrups, lozenges etc. The excipients which can be used may be selected from starch, di-calcium phosphate, polysorbate, fumed silica, etc, The food stuffs in which the synergistic herbal composition may be used as a dietary supplement/food additive is selected from the group comprising bread, pizza, health drinks, biscuits, chocolates, pasta etc.

The present invention also provides a process for preparing the phytochemical composition, comprising:
a. extracting curcuminoids from rhizome of *Curcuma longa*;
b. extracting the rhizomes of *Curcuma longa* from step 'a' using water.
c. concentrating the extract and spray drying the concentrated liquid extract to get powdered water extract; and
d. mixing the water extract obtained from step 'c' and oil of *Curcuma longa* to yield the synergistic composition derived from *Curcuma longa*.

Water extract obtained from the step 'd' can be added to organic solvents to obtain the supernatant as F2 (polysaccharide less fraction) and the sediment as F1 (polysaccharide rich fraction), A preferred aspect of the process comprises;
a. extracting curcuminoids from rhizome of *Curcuma longa*;
b. recovering solvents from the raw material bed;
c. extracting the rhizomes of *Curcuma longa* left after steps 'a' and 'b' using water by maceration at room temperature and followed by refluxing.
d. concentrating the water extract by distillation under vacuum to achieve total solid content of 15-35% w/v;
e. spray drying the concentrated liquid extract to get powdered water extract;
f. precipitating curcuminoids from the extraction liquid obtained from step 'a' using suitable solvents and obtaining curcumin removed turmeric oleoresin;
g. distilling the curcumin removed numeric oleoresin using steam or by high vacuum distillation to get *Curcuma longa* oil: and
h. mixing the water extract obtained from step V and the oil obtained from step 'g' to obtain the composition.

Water extract obtained from the step 'h' may be fortified with 5 volumes of ethanol and centrifuged to obtain the supernatant as F2 (polysaccharide less fraction) and the sediment stirred with 5 volumes of ethanol to obtain F1 (polysaccharide rich fraction).

Extraction of curcuminoids from the rhizome of *Curcuma longa* is carried out using the established procedures known in the industry which includes solvent extractions using acetone, dichloroethane, dichloromethane, methanol, ethylacetate, methyl ethyl ketone, toluene or mixtures of these solvents. The step of recovering solvents from the raw material bed is carried out using standard techniques like steam stripping. Further, solvents used for precipitating curcuminoids from oleoresin may be selected from the group comprising isopropyl alcohol and methanol.

Additionally, the present invention also provides use of the phytochemical composition in inhibiting $PGE_2$, IL-12, and stimulation of IL-10 activity which results in anti inflammatory effect and in prevention and treatment of osteoarthritis.

The present invention further provides a method for preventing and treating osteoarthritis in a subject comprising administering a pharmaceutically effective amount (e.g. 0.1-2 gm/day) of the composition. Pharmaceutically acceptable additives may be administered at the same time, in the same or separate products. The composition may be administered in any suitable dosage form, including capsules, tablets, syrups, lozenges, etc.

The composition of the present invention is generally non-toxic with limited side effects.

The present invention is explained further in the following specific examples which are only by way of illustration and are not to be construed as limiting the scope of the invention.

EXAMPLES

Example 1

Preparation of the Composition 100 g of powdered *Curcuma longa* rhizomes are taken and refluxed with 400 ml of acetone or ethyl acetate for 2 hours. The liquid extract is filtered and marc extracted two more times with acetone or ethyl acetate in the same manner. The acetone or ethyl acetate soluble part (combined three washes) is concentrated by distillation under vacuum and the curcuminoids removed from the extract by precipitation and crystallization with isopropyl alcohol to yield curcumin removed oleoresin, Curcumin removed oleoresin is distilled by passing steam and the steam distillate and separate oil layer are collected.

The acetone or ethyl aceate insoluble part of rhizomes, which is almost free from curcuminoids, is refluxed with water. The liquid water extract is collected by filtration and the marc extracted two more times with water in the same manner. The liquid water extract (combined from three washes) is concentrated by distillation under vacuum to have about 20 to 35% total solids. The concentrated liquid extract is spray dried to get a powdered water extract. The powdered water extract is mixed with the oil in 99:1 proportion in a blender and sieved through 60 mesh to get the water extract of *Curcuma longa* (CL).

*Curcuma longa* water extract was added to 5 volumes of water and the resulting suspension was fortified with 5 volumes of ethanol. The above contents were centrifuged. The supernatant obtained was concentrated under reduced pressure to get fraction F2 (polysaccharide less fraction). The sediment obtained after centrifugation was stirred with 5 volumes of ethanol at room temperature. The precipitate obtained was dried under vacuum to obtain fraction F1 (polysaccharide rich fraction).

Example 2

Data on Synergy of Present Composition

Relevance of Lymphocyte Proliferation assay: The lymphocyte proliferation assay (LPA) is used to identify the possible immunostimulatory or immunosuppressant effects of various natural products (drags) on isolated whole murine splenocytes (Namgoong, et al., 1994, Lee, et al., 1995, and Koch, et al., 2001). Overall, the body's immune response has one primary function: to protect the body from an object that the body does not recognize as a normal object. The immune response can be either normal or abnormal. Inflammation is also one of the body's first responses to infections as the body tries to rush immune cells and cytotoxic chemicals to the infected tissue to defend against the infections or foreign particles. Arthritis tends to develop inflammation in the joints and their surrounding tissues.

Summary of the study: Successive water extract of *C. longa* and the composition of the invention showed significant increase at the tested concentrations. The $EC_{50}$ value of successive water extract of *C. longa* and the composition of the invention were found to be ~7 μg/mL and ~4 μg/mL respectively. *C. longa* oil showed increase in splenocyte number at a concentration of 0.8 μg/mL to 1.6 μg/mL followed by decrease in subsequent concentrations. The composition of the invention showed 2 times more potent activity compared to successive water extract of *C. longa* whereas *C. longa* oil did not show similar activity at the tested concentrations. This explains the synergistic activity of the composition of the invention. From the above study, the immunomodulatory potential of the successive water extract of *C. longa, C, longa* oil and the composition of the invention are in the following order: composition of the instant invention>successive water extract>oil fraction.

Example 3

Effect of Water Extract of *C. longa. C, longa* oil and the Composition of the Invention on IL-12 Levels in LPS Induced Murine Splenocytes Relevance of Interleukin-12 assay: IL-12 is an important mediator of inflammatory diseases such as psoriasis, multiple sclerosis, rheumatoid arthritis and Crohn's diseases. IL-12 plays a role in inflammatory cell recruitment via PMN production of IL-8, the most potent chemokine for PMNs themselves. IL-12, produced early dining the response to infectious agents, could thus promote rapid IL-8-induced PMN influx (Ethuin et al., 2001). Recent attention has turned towards IL-12 family of cytokines as a promising area of study for inflammation associated diseases and inhibition of this cytokine synthesis may have therapeutic applications (Katrina, et al., 2009).

Summary of the Study: In this study, the effect of successive water extract of *C. longa, C. longa* oil and the composition of the invention was evaluated on the release of IL-12 levels in LPS treated murine splenocytes. Water extract of *C. longa, C. longa* oil and the composition of the invention showed significant dose dependent inhibition of LPS induced IL-12 levels in murine splenocytes. The $EC_{50}$ values of water extract of *C. longa, C. longa* oil and the composition of the invention was found to be 3 μg/mL, 13 μg/mL and 2 μg/mL respectively. From the above results, it can be concluded that inhibition of LPS induced IL-12 release of the composition of the invention is mainly attributed to water extract of *C. longa*.

Example 4

Effect of the Composition of the Invention on IL-10 Levels in Naive Murine Splenocytes Relevance of assay: IL-10 is a potent and broad-spectrum anti-inflammatory cytokine, secreted by diverge category of cells. It is capable of inhibiting the synthesis of pro-inflammatory cytokines like IFN-gamma, IL-2, IL-3, TNF-alpha and GM-CSF by blocking NF-kappa B activity (Siebenlist, et al., 1994).

Summary of experiment: The effect of the composition of the invention was evaluated on the release of IL-10 levels in murine splenocytes. Composition of the invention exhibited significant dose dependent increase in IL-10. The $EC_{50}$ value of composition of the invention was found to be ~52 μg/mL.

From the above results, it can be concluded that composition of the invention has antiinflammatory activity by inducing IL-10 release from murine splenocytes Example 5

Effect of the Composition of the Invention on LPS Induced $PGE_2$ Level in Mouse Splenocytes Relevance of $PGE_2$ assay: The cyclooxygenase (COX) pathway is a major route for metabolism of arachidonic acid (AA), which is converted to cyclic prostaglandins (PGG and PGH) and subsequent metabolic products such as $PGE_2$ and $PGD_2$ (Halliwell, et al., 2004). It has been postulated that $PGE_2$ is a necessary intermediate in the acute inflammatory response and thus can serve as an excellent target for inflammatory conditions like osteoarthritis (Molloy and McCarthy, 2005; Fahmi 2004) and inflammation associated disorders (Williams, et al., 1999; Hata and Breyer, 2004; Yedgar, et al., 2006).

Summary of experiment: The effect of the composition of the invention was studied in LPS induced $PGE_2$ release in murine splenocytes. The composition of the invention showed significant dose dependent inhibition of LPS induced $PGE_2$ levels in murine macrophage cells. The $EC_{50}$ value of the composition of the invention was found to be 174 μg/mL, In conclusion, composition of invention showed anti-inflammatory activity by reducing LPS induced $PGE_2$ levels.

Example 6

Effect of the Composition of the Invention on IL-12 Levels in LPS Induced Marine Splenocytes Relevance of Interleukin-12 assay: IL-12 is an important mediator of inflammatory diseases such as psoriasis, multiple sclerosis, rheumatoid arthritis and Crohn's diseases. IL-12 plays a role in inflammatory cell recruitment via PMN production of IL-8, the most potent chemokine for PMNs themselves. IL-12, produced early during the response to infectious agents, could thus promote rapid IL-8-induced PMN influx (Ethuin et al, 2001). Recent attention has turned towards IL-12 family of cytokines as a promising area of study for inflammation associated diseases and inhibition of this cytokine synthesis may have therapeutic applications (Katrina, et al., 2009).

Summary of the Study: In this study, the effect of the composition of the invention was evaluated on the release of IL-12 levels in LPS treated murine splenocytes. The composition of the invention showed significant dose dependent inhibition of LPS induced IL-12 levels in murine splenocytes. The $EC_{50}$ value of the composition of the invention was found to be 2 μg/mL. From the above result, it can be seen that inhibition of LPS induced IL-12 release of the composition of the invention is mainly attributed to its antiinflammatory property.

Based on Examples (3-6), it can be seen mat the mechanism of anti-inflammatory activity of the composition of the invention is due to 1. Stimulation of IL-10 release
2. Inhibition of PGE$_2$ release
3. Inhibition of IL-12 release

Example 7

Evaluation of Anti-Inflammatory Activity of the Composition of the in Xylene Induced Ear Edema Model using Albino Swiss Mice Summary of Xylene induced ear edema model using albino Swiss mice: The objective of this study is to evaluate the anti-inflammatory activity of the composition of the invention in xylene induced ear edema model, when administered as a single oral dose to male albino Swiss mice. The composition of the invention at all the tested doses (90, 180 and 360 mg/kg) showed significant anti-inflammatory activity as compared to vehicle control group. Based on the findings of this study, it can be stated that the composition of the invention revealed significant anti-inflammatory activity at ail the tested dose levels, with optimal activity observed at 90 mg/kg in xylene induced ear edema model in Swiss albino mice.

Example 8

Evaluation of Anti-Inflammatory Activity of the Composition of the Invention in Cotton Pellet Granuloma Model using Albino Wistar Rats Cotton pellet granuloma model using albino Wistar rats: The present study was undertaken to evaluate the anti-inflammatory activity of the composition of the invention in cotton pellet granuloma model using albino Wistar rats. The composition of the invention at doses of 45, 90 and 180 mg/kg significantly reduced both wet and dry weights of the cotton pellets as compared to vehicle control group. Based on the results of the present study, it can be stated that the composition of the invention revealed significant anti-inflammatory activity at all the tested doses, with optimal anti-inflammatory activity observed at 45 mg/kg in cotton pellet granuloma model using albino Wistar rats.

Example 9

Acute Oral Toxicity Study of the Composition of the Invention in Albino Wistar Rats Acute oral toxicity study of the composition of the invention was conducted in female albino Wistar rats. Administration of the composition of the invention at the higher dose level of 5000 mg/kg, b.w. showed neither mortality nor abnormal clinical signs. Overall weight gain of treated animals was found to be normal during the study duration. On necropsy, no major gross pathological changes were observed in any of the treated rats. From these results, it is concluded that the composition of the invention was found to be sale as a single dose oral administration to female albino Wistar rats up to 5000 mg/kg, b.w.

Example 10

Salmonella Reverse Mutation Assay for the Composition of the Invention

Salmonella reverse mutation assay: Salmonella reverse mutation assay was conducted to test the mutagenic potential of the composition of the invention using *S. typhimurium* tester strains viz., TA98 and TAMix. The composition of the invention was tested at the concentrations of 5000 µg/ml, 1510 µg/ml and 450 µg/ml, 140 µg/ml, 40 µg/ml and 10 µg/ml using phosphate buffered saline (PBS) as solvent and with and without the metabolic activation (S9 fraction).

The composition of the invention did not induce mutation both in the presence and absence of metabolic activation in *S. typhimurium* mutant strains TA98 and TAMix at all the concentrations tested. This study suggests that the composition of the invention is non-mutagenic up to a concentration of 5000 µg/ml.

Example 11

Clinical Studies

Safety and efficacy of the composition of the invention in the treatment of painful osteoarthritis: a randomized, single blind, placebo-controlled trial The present trial was earned out to evaluate the effectiveness of the composition of the invention in the treatment of painful OA [a randomized, single blind, placebo-controlled trial]. 120 patients (37 males and 83 females) with primary OA received either the composition of the invention (500 mg twice daily) or Glucosamine sulphate (750 mg twice daily) or placebo (500 mg twice daily) or combination of the composition of the invention and Glucosamine sulphate for 42 days. During the treatment period two follow up visits on day $21^{st}$ and day $42^{nd}$, efficacy was evaluated in terms of change in the intensity/severity of symptoms (as measured by VAS, WOMAC scale) and examination by orthopaedician (as measured by CGIC). The analysis of scores of all symptoms (over the period) in the composition of the invention treated group after $21^{st}$ and $42^{nd}$ days of treatment, were found to be significantly decreased when compared to placebo group (WOMAC-$p<0.05$; VAS-$p<0.05$; CGIC-$p<0.001$). Similarly, the composition of the invention treated group showed remarkable decrease in the use of rescue medication ($p<0.05$) along with clinical and subjective improvement in comparison to the placebo group.

Overall improvement in signs and symptoms of OA were also seen with Glucosamine sulphate and its combination with the composition of the invention.

Treatment with the composition of the invention was found to be safe and well tolerated by all patients during the intervention period.

The above findings demonstrate the efficacy of the composition of the invention and that it could possibly he a safer and effective option for the treatment of patients with primary painful knee OA.

Example 12

Efficacy Data on F1 and F2 Proliferation of Unstimulated Mouse Splenocytes (FIG. 1)

Effect of *Curcuma longa* (CL), F1 and F2 on proliferation of unstimulated mouse splenocytes. Mouse splenocytes were treated with CL or F1 or F2 at the indicated concentrations without LPS and further incubated for 48 h. The splenocyte numbers were increased dose-dependently by CL, F1 and F2. Values are expressed as percentage of LPS control (Untreated and LPS treated splenocyte number were taken as 0 and 100% respectively). Overall, CL and F1 exhibited potent bioactivity while F2 was weakly active.

Example 13

Figure 2:
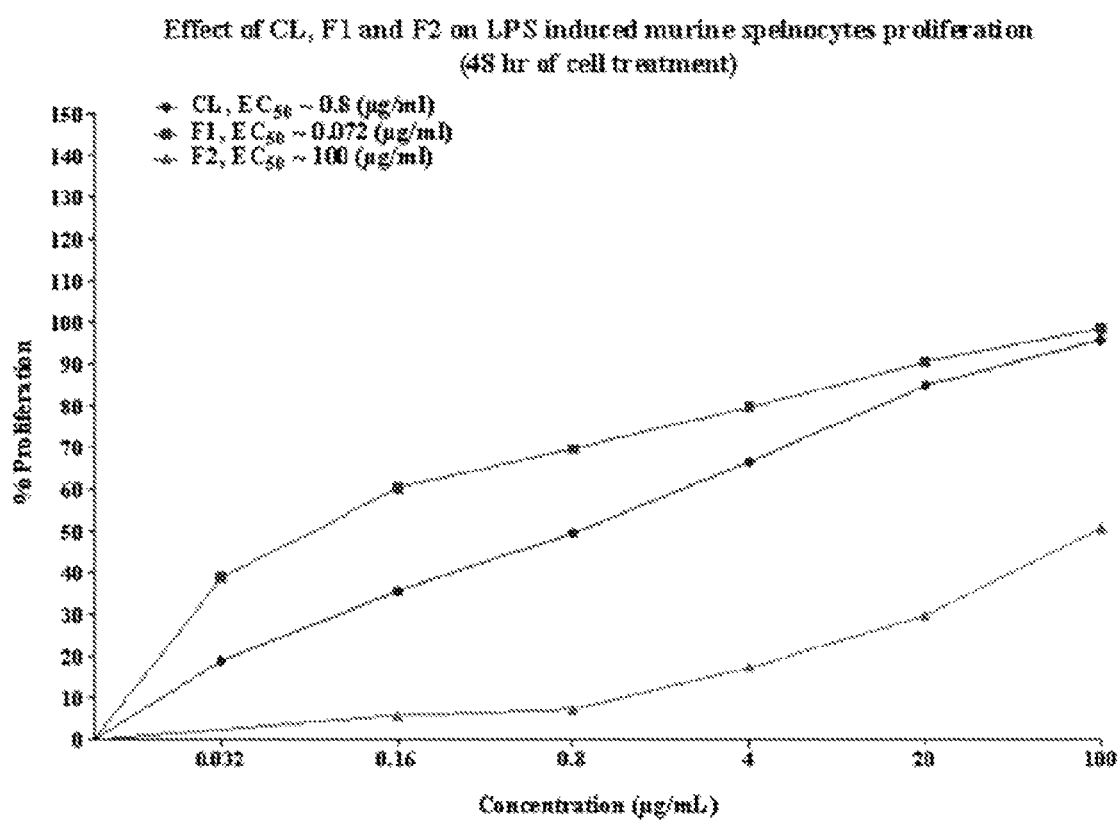
FIG. 2: Effect of CL, F1 and F2 on LPS induced murine splenocyte proliferation.

Efficacy Data on F1 and F2 Proliferation of LPS Mouse Splenocytes (FIG. 2)

Effect of *Curcuma longa* (CL), F1 and F2 on proliferation of LPS stimulated mouse splenocytes. Mouse splenocytes were treated with CL or F1 or F2 at the indicated concentrations with LPS and further incubated for 48 h. The splenocyte numbers were increased dose-dependently by CL, F1 and F2. Values are expressed as percentage of LPS control (LPS at concentrations of 5 µg/mL and 10 µg/mL. treated splenocyte number were taken as 0 and 100% respectively). Overall, CL and F1 exhibited potent bioactivity while F2 was weakly active.

Example 14

Figure 3:
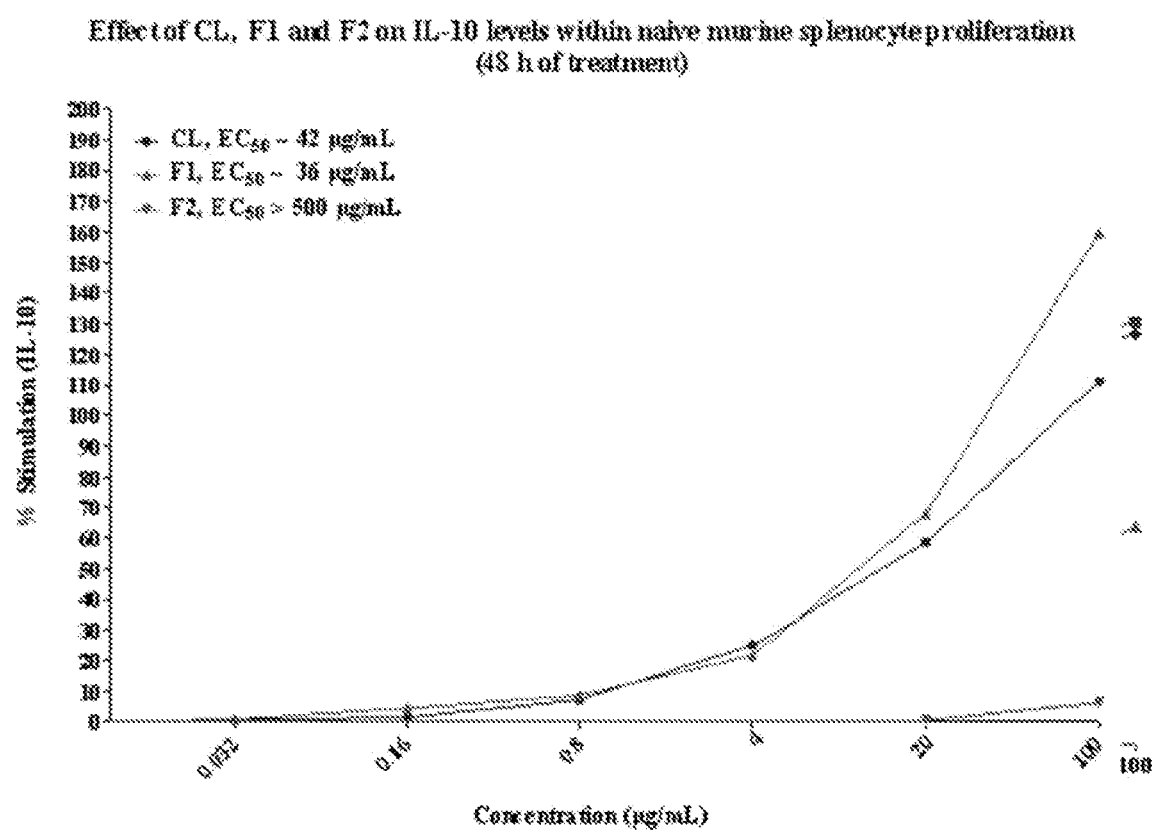
FIG. 3: Effect of CL, F1 and F2 on IL-10 levels within naive murine splenocyte proliferation.

Efficacy Data of F1 and F2 on IL-10 Expression in Unstimulated Mouse Splenocytes (FIG. 3)

Figure 4:
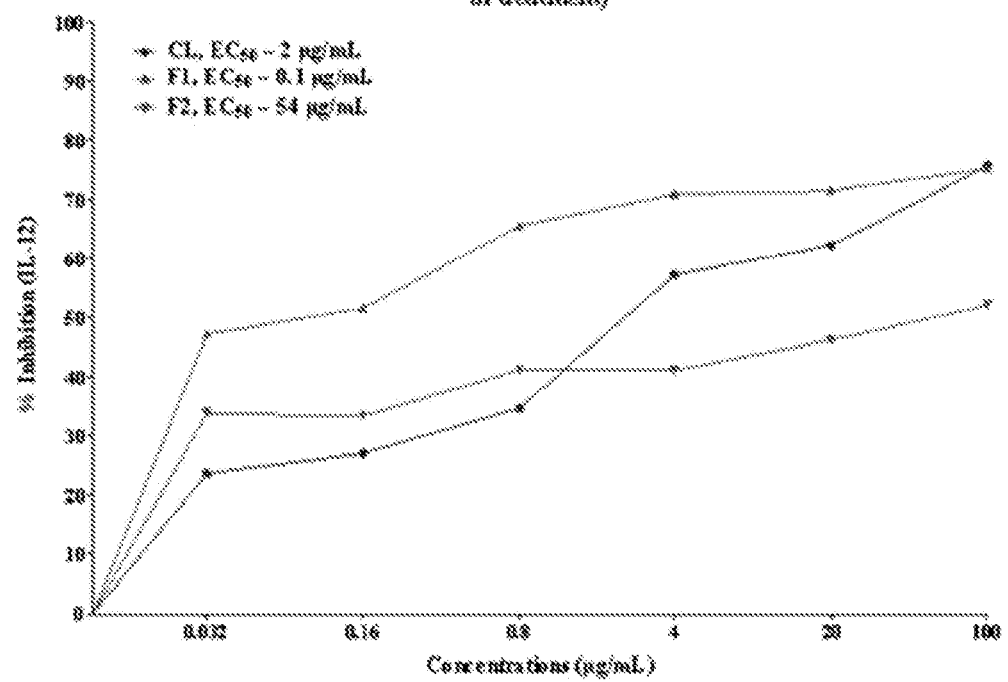
FIG. 4: Effect of CL, F1 and F2 on IL-12 levels within LPS induced murine splenocyte proliferation.

Effect of *Curcuma longa* (CL), F1 and F2 on IL-10 expression in unstimulated mouse splenocytes (FIG. 4). Mouse splenocytes were treated with CL or F1 or F2 at the indicated concentrations and further incubated for 48 h. After 48 h, the cells were centrifuged and the supernatants were collected for IL-10 estimation and the values are expressed as percentage stimulation (Untreated and LPS stimulated IL-10 expression were taken as 0 and 100% respectively). Overall, CL and F1 exhibited potent bioactivity while F2 was weakly active.

Example 15

Efficacy Data of F1 and F2 on LPS Induced IL-12 expression in mouse splenocytes (FIG. 4)

Effect of *Curcuma longa* (CL), F1 and F2 on LPS induced IL-12 expression in mouse splenocytes. Mouse splenocytes were treated with CL or F1 or F2 at tire indicated concentrations with LPS and further incubated for 48 h. After 48 h, the cells were centrifuged and the supernatants were collected for IL-12 estimation and the values are expressed as percentage inhibition (Untreated and LPS stimulated IL-12 expression were taken as 0 and 100% respectively). Overall, CL and F1 exhibited potent bioactivity while F2 was weakly active.

Example 16

Figure 5:
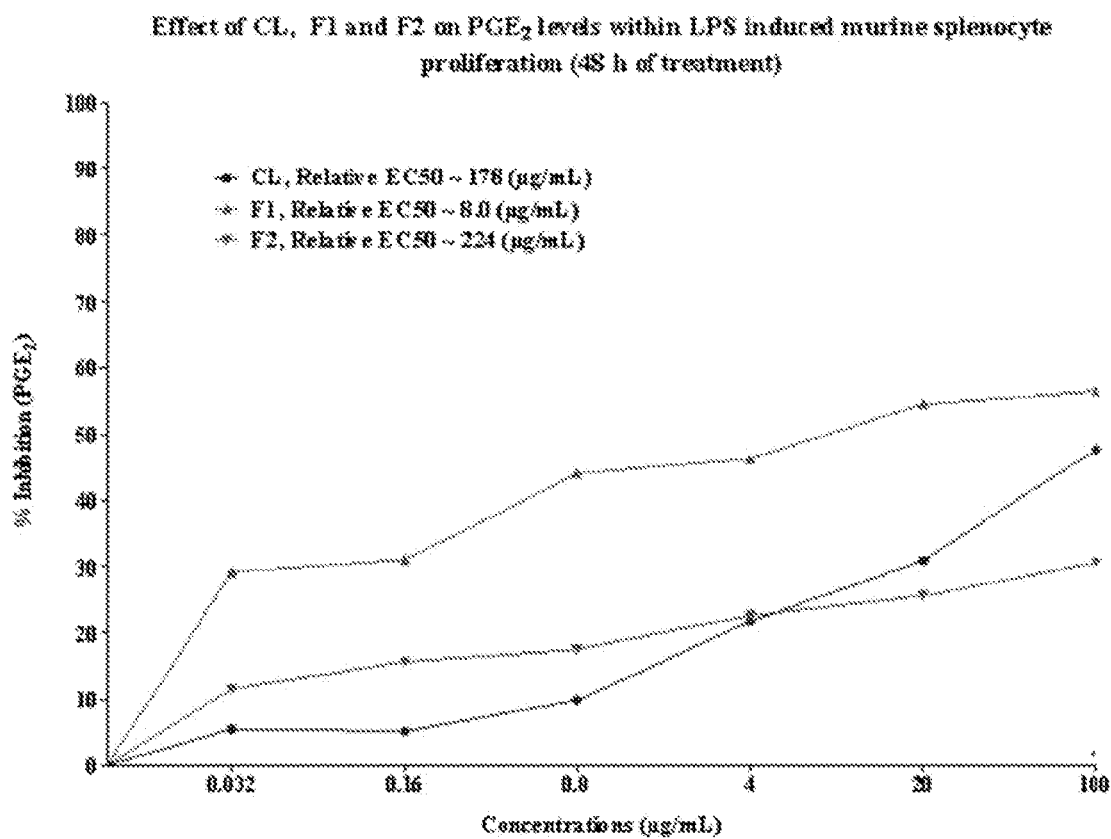
FIG. 5: Effect of CL, F1 and F2 on $PGE_2$ levels within LPS induced murine splenocyte proliferation.

Efficacy Data of F1 and F2 on LPS Induced $PGE_2$ Expression in Mouse Splenocytes (FIG. 5)

Effect of *Curcuma longa* (CL), F1 and F2 on LPS induced $PGE_2$ expression in mouse splenocytes. Mouse splenocytes were treated with CL or F1 or F2 at the indicated concentrations with LPS and further incubated for 48 h. After 48 h, the cells were centrifuged and the supernatants were collected for $PGE_2$ estimation and the values are expressed as percentage inhibition (Untreated and LPS stimulated $PGE_2$ expression were taken as 0 and 100% respectively). Overall, CL and F1 exhibited potent bioactivity while F2 was weakly active.

I claim:

1. A pharmaceutical composition, comprising:
    a mixture of *Curcuma longa* water extract and *Curcuma longa* oil; and
    a pharmaceutically acceptable carrier,
    wherein the pharmaceutical composition does not include curcuminoids, wherein the *Curcuma longa* water extract and *Curcuma longa* oil are present in amounts effective for treating osteo-arthritis and pain associated therewith in a subject, and the amounts of the *Curcuma longa* water extract and *Curcuma longa* oil are 99% by weight and 1% by weight, respectively, of the mixture.

2. The composition as claimed in claim 1, wherein the water extract is prepared from marc left after extracting curcuminoids from *Curcuma longa*.

3. The composition as claimed in claim 1, further comprising polysaccharides derived from *Curcuma longa*.

4. The composition as claimed in claim 3, further comprising F1 and F2 fractions, wherein the F1 and F2 fractions are obtained by sequentially processing the water extract, wherein the F1 fraction is a polysaccharide rich fraction as compared to the F2 fraction.

5. The composition as claimed in claim 1, further comprising glucosamine.

6. The composition as claimed in claim 1, wherein the pharmaceutically acceptable carrier is selected from the group consisting of granulating agents, binding agents, lubricating agents, disintegrating agents, sweetening agents, coloring agents, flavouring agents, coating agents, plasticizers, preservatives, suspending agents, emulsifying agents and spheronization agents.

7. The composition as claimed in claim 1, wherein the composition is formulated into a dosage form selected from the group consisting of capsules, tablets, syrups, lozenges, troches, elixirs, phytoceuticals and neutraceuticals.

8. A process for preparing the pharmaceutical composition as claimed in claim 1, comprising:
    (a) extracting rhizomes of *Curcuma longa* using water so as to obtain a liquid extract;
    (b) concentrating the liquid extract obtained in step (a) so as to obtain a concentrated liquid extract and spray drying the concentrated liquid extract to obtain a powdered water extract; and
    (c) mixing the powdered water extract obtained from step (b) and oil of *Curcuma longa* to yield the pharmaceutical composition.

9. The process as claimed in claim 8, wherein the powdered water extract obtained from the step (b) is added to organic solvents to obtain a supernatant as F2 (polysaccharide less fraction) and a sediment as F1 (polysaccharide rich fraction).

10. A process for preparing the composition as claimed in claim 1, comprising:
    (a) extracting curcuminoids from rhizomes of *Curcuma longa*;
    (b) recovering solvents from a raw material bed;
    (c) extracting the rhizomes of *Curcuma longa* left after steps (a) and (b) using water by maceration at room temperature and followed by refluxing to obtain a water extract;
    (d) concentrating the water extract obtained in the step (c) by distillation under vacuum to obtain a concentrated liquid extract and achieve a total solid content of 15-35% w/v;
    (e) spray drying the concentrated liquid extract to obtain a powdered water extract;
    (f) precipitating the curcuminoids from an oleoresin obtained from step (a) using a solvent and obtaining a curcumin removed turmeric oleoresin;
    (g) distilling the curcumin removed turmeric oleoresin using steam or by high vacuum distillation to obtain *Curcuma longa* oil; and
    (h) mixing the powdered water extract obtained from step (e) and the oil obtained from step (g).

11. The process as claimed in claim 10, wherein the powdered water extract obtained from the step (h) is fortified with 5 volumes of ethanol and centrifuged to obtain a supernatant as F2 (polysaccharide less fraction) and a sediment that is stirred with 5 volumes of ethanol to obtain F1 (polysaccharide rich fraction).

12. The process as claimed in claim 10, wherein the step of recovering the solvents from the raw material bed is done by steam stripping.

13. The process as claimed in claim 10, wherein curcuminoids are precipitated from the oleoresin using solvents selected from the group consisting of isopropyl alcohol, methanol, ethanol, and a mixture of two or more of these solvents.

14. A food product comprising the composition as claimed in claim 1.

15. The food product as claimed in claim 14, selected from the group consisting of bread, nutritional bars, cookie, beverage, pizza, health drinks, biscuits, chocolates and pasta.

16. A dietary or food supplement comprising the composition as claimed in claim 1.

\* \* \* \* \*